United States Patent [19]  [11] 3,969,351
Narayanan et al. [45] July 13, 1976

[54] MORPHOLINE CONTAINING ISOTHIOCYANOBENZOXAZOLES

[75] Inventors: Venkatachala L. Narayanan, Hightstown; Glenn Anthony Jacobs, Princeton; Rudiger D. Haugwitz, Titusville, all of N.J.

[73] Assignee: E. R. Squibb & Sons, Inc., Princeton, N.J.

[22] Filed: May 15, 1975

[21] Appl. No.: 577,587

Related U.S. Application Data

[63] Continuation-in-part of Ser. No. 471,083, May 17, 1974, abandoned.

[52] U.S. Cl............... 260/247.1 H; 424/246; 424/248; 424/250; 424/267; 424/272; 260/243 B; 260/268 BC; 260/293.57; 260/293.58; 260/307 D; 260/332.3 R
[51] Int. Cl.².................................. C07D 413/14
[58] Field of Search............260/247.1 H, 243 B

[56] References Cited
UNITED STATES PATENTS
3,849,431  11/1974  Gallay et al.................. 260/247.1 H Primary Examiner—Natalie Trousof
Assistant Examiner—R. W. Ramsuer
Attorney, Agent, or Firm—Lawrence S. Levinson; Merle J. Smith; Donald J. Barrack

[57] ABSTRACT

Isothiocyanobenzoxazoles having the structure

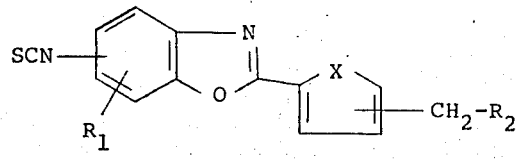

wherein $R_1$ is hydrogen, alkyl, alkoxy, or halogen; X is O or S; $R_2$ is 1-pyrrolidinyl, 1-piperidinyl, 4-morpholinyl, 4-thiamorpholinyl, 4-alkyl-1-piperazinyl, 4-akyl-1-piperidinyl or 3-alkyl-1-pyrrolidinyl, are useful anthelmintic agents.

8 Claims, No Drawings

MORPHOLINE CONTAINING ISOTHIOCYANOBENZOXAZOLES

This application is a continuation-in-part of copending U.S. patent application Ser. No. 471,083, filed May 17, 1974, now abandoned.

SUMMARY OF THE INVENTION

Isothiocyanobenzoxazoles having the structure

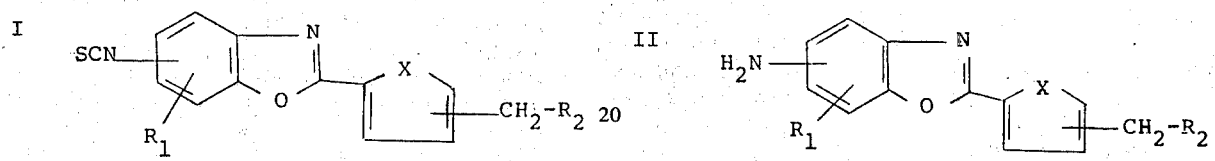

have useful anthelmintic activity. In formula I, and throughout the specification the symbols are as defined below:

$R_1$ can be hydrogen, alkyl, alkoxy or halogen;
X can be oxygen or sulfur; and
$R_2$ can be 1-pyrrolidinyl, 1-piperidinyl, 4-morpholinyl, 4-thiamorpholinyl, 4-alkyl-1-piperazinyl, 4-alkyl-1-piperidinyl or 3-alkyl-1-pyrrolidinyl.

The term "alkyl" as used throughout the specification refers to straight and branched chain aliphatic hydrocarbon groups having 1 to 6 carbon atoms. Exemplary groups are methyl, ethyl, propyl, isopropyl, butyl, t-butyl, pentyl, hexyl, isohexyl and the like. Those alkyl groups having 1 to 3 carbon atoms are preferred.

The term "alkoxy" as used throughout the specification refers to groups of the structure Z—O— wherein Z is alkyl as defined above.

The term "halogen" as used throughout the specification refers to fluorine, chlorine, bromine and iodine; chlorine and bromine are the preferred halogens.

DETAILED DESCRIPTION OF THE INVENTION

Isothiocyanobenzoxazoles of formula I, and their pharmaceutically acceptable acid addition salts, are useful for the treatment of mammals, e.g. sheep, dogs, cats, etc., infected with helminths. More specifically, the compounds of formula I are active taeniacidal agents useful in treating tapeworms such as *Hymenolepis nana*. In treating animals infected with tapeworms, the isothiocyanobenzoxazoles of this invention can be mixed with a pharmaceutically acceptable carrier to form a feed supplement which can be incorporated in the animal feed in the desired concentration. Alternatively, the water soluble salts of the isothiocyanobenzoxazoles can be added to the drinking water of the animals being treated. The preferred dosage level for treating a tapeworm infection will depend to a large extent on the particular isothiocyanobenzoxazole compound being employed, on the severity of the infection, and on the particular mammalian species being treated. In general, however, the isothiocyanobenzoxazoles of formula I exhibit taeniacidal activity when administered to animals in a daily dose of from about 25 to about 300 milligrams per kilogram of body weight. It is preferred to employ the compounds of this invention in the dosage range of about 50 to 200 milligrams per kilogram per day. The compounds may be given in a single dose or divided into a plurality of smaller doses. If desired, the course of treatment may be extended over a period of days, in which case the optimum daily dose level may be lowered.

The isothiocyanobenzoxazoles of formula I are prepared by reacting a benzoxazole having the structure

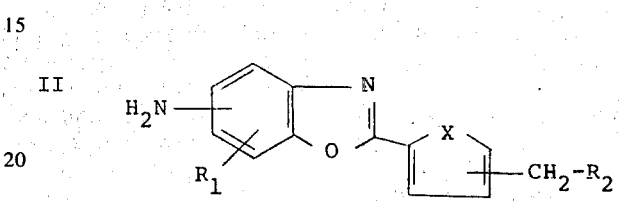

with a reagent capable of converting the amino substituent into an isothiocyano group. The reaction is carried out in the presence of a solvent which is inert to the reactants, e.g., aromatic solvents such as benzene or toluene, halogenated hydrocarbons such as chloroform, or ethers such as glyme.

Thus, for example, an aminobenzoxazole of formula II can be converted to an isothiocyanobenzoxazole of formula I by reacting it with a thiocarbonic acid derivative having the formula $$R_3\text{—CS—}R_4 \qquad \text{III}$$

wherein $R_3$ is chlorine or bromine; and $R_4$ is chlorine, bromine or a dialkylamino group such as diethylamino. Thiophosgene and N,N-diethylthiocarbamoyl chloride are exemplary of the compounds of formula III.

When thiophosgene is employed in the above reaction, the reaction is carried out at a temperature in the range of from about 0°C to about 60°C, preferably in the presence of an acid binding agent such as calcium or sodium carbonate or an amine such as triethylamine. The reaction with thiophosgene is further described in Houben-Weyl's *Methoden Der Organischen Chemie*, 4th Edition, Vol. 9, pages 867 and *ff* (1955). The use of the acid binding agents is further described by O. E. Schultz in Arch. Pharm. 295, 146–151 (1962).

When N,N-diethylthiocarbamoyl chloride is employed to react with a compound of formula II, the reaction is carried out at a temperature ranging from about 40°C to about 200°C as described in the procedure set forth in J. Org. Chem. 30, 2465 (1965).

Isothiocyanobenzoxazoles of formula I can also be prepared by reacting an aminobenzoxazole of formula II with carbon disulfide in the presence of an organic or inorganic base, whereby the amino group is first converted into the corresponding dithiocarbamic salt which is subsequently dehydrosulfurized to the isothiocyano group. The dehydrosulfurization can be performed oxidatively with metal salts (for a further description see British Pat. No. 793,802 and Dutch Pat. No. 81,326), e.g., lead copper, zinc, or ferric salts; with iodine; with alkali metal (preferably sodium or potassium) hypochlorites (for description see French Pat. No. 1,311,855); or with suitable acid halides such as phosgene and phosphorous oxychloride (see D. Martin et al., Chem. Ber. 98, 2425–2426 (1965)); or with chlorine and ammonium sulfide (see Deutsche Auslegungsschrift No. 1,192,189); or with chloramine T (see British Pat. No. 1,024,913).

Another method for preparing an isothiocyanobenzoxazole of formula I comprises reacting an aminobenzoxazole of formula II with phosgene and phosphorous pentasulfide according to the procedure set forth in Houben-Weyl, *Methoden Der Organischen Chemie*, 4th Edition, Vol. 9, pages 867 and *ff* (1955).

Still another method for preparing the isothiocyanobenzoxazoles of formula I comprises reacting an aminobenzoxazole of formula II with ammonium rhodanide and benzoyl chloride to yield the thiourea derivative which may then be thermally decomposed, e.g., in boiling chlorobenzene, to the isothiocyano derivative. A further description of the reaction may be found in Houben-Weyl, *Methoden Der Organischen Chemie*, 4th Edition, Vol. 9, pages 867 and *ff* (1955).

Still another method for preparing the isothiocyanobenzoxazoles of formula I comprises reacting an aminobenzoxazole with carbon disulfide and dicyclohexylcarbodiimide in the presence of a tertiary amine according to the procedure set forth by J. C. Jochims, Chem. Ber. 101, 1746 (1968).

The aminobenzoxazoles of formula II can be prepared from the corresponding nitro compounds having the structure IV 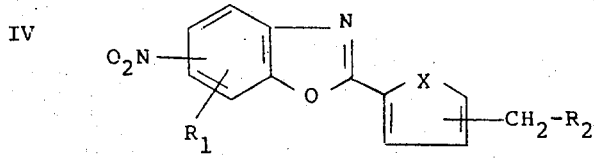

Reduction of a nitrobenzoxazole of formula IV to an aminobenzoxazole of formula II is accomplished using procedures well known in the art. Exemplary of such procedures is catalytic hydrogenation using, for example, palladium or platinum oxide as the catalyst.

The nitrobenzoxazoles of formula IV are prepared from the corresponding compound of the structure V 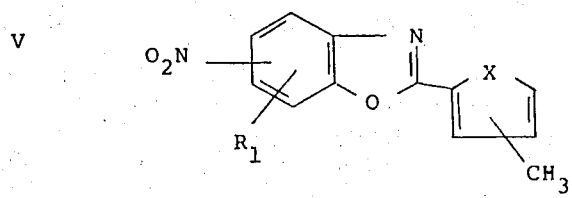

by first treating it with N-bromosuccinimide or N-chlorosuccinimide in the presence of a catalyst such as sodium peroxide or azobisbutyronitrile to yield a compound having the structure VI 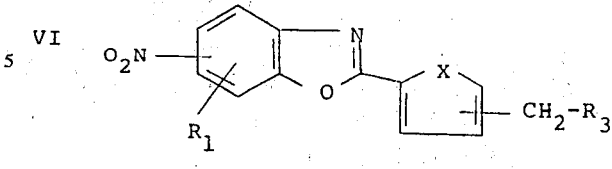

wherein $R_3$ is chloro or bromo. The compound of formula VI is then reacted with an excess of a heterocyclic compound ($R_2$—H) at an elevated temperature to yield the nitrobenzoxazole of formula IV.

Alternatively, the nitrobenzoxazoles of formula IV, wherein the —$CH_2$—$R_2$ group is in the alpha position, can be prepared by reacting a compound having the structure VII 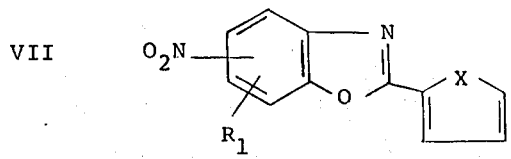

with formaldehyde and a heterocyclic compound ($R_2$—H) using a Mannich reaction. The Mannich reaction is well known in the art, see for example:
1. F. F. Bliche, Organic Reactions, 1, 303 (1942).
2. B. Reichert, Die Mannich Reaktion, Springer Verlag, Berlin (1959).
3. H. Hellmann & G. Optiz, Angew Chem., 68, 265, (1956).

The compounds of formula V and VII are synthesized using procedures known in the art. The processes are set forth in the following references:
1. The most general procedure (A. Ladenburg, Ber., 1876, 9, 1524: M. A. Phillips, J. Soc. Chem. Ind., 1937, 56, 474) comprises heating o-aminophenols with carboxylic acids, their chlorides, anhydrides or other derivatives including aldehydes, amides (St. von Niementowski, Ber. 1897, 30, 3064: S. Skraup, Ann., 1919, 419, 80; Ber., 1922, 55, 1097), nitriles (E. L. Holljes and E. C. Wagner, J. Org. Chem., 1944, 9, 31), amidines (E. C. Wagner, ibid., 1940, 5, 133) and iminoether hydrochlorides (F. E. King and R. M. Acheson, J. Chem. Soc., 1949, 1396).
2. The anti-oximes of o-hydroxyphenylketones yield benzoxazoles as products of Beckmann transformations (see J. Meisenheimer, et al., J. Pr. Chem., 1928, [ii], 119, 315).
3. 2-Arylbenzoxazoles are produced by lead tetraacetate oxidation of Schiff's bases derived from o-aminophenols and arylaldehydes (F. Stephens and J. D. Bower, J. Chem. Soc., 1949, 2917; 1950, 1722).
4. Interaction of p-nitrophenylazides with acetic and polyphosphoric acids leads to 2-methyl-6-nitrobenzoxazoles. (R. Garner, et al., J. Chem. Soc., 1960, 1980).

The pharmaceutically acceptable acid addition salts of the compounds of formula I can be prepared using procedures well known in the art. Exemplary of the salts contemplated for use in this invention are hydrohalides (e.g., the hydrochloride and hydrobromide), sulfate, nitrate, tartrate, phosphate, maleate, fumarate, citrate, succinate, methanesulfonate, benzenesulfonate, toluenesulfonate, and the like.

Compounds of formula I wherein $R_1$ is hydrogen are preferred.

Compounds of formula I wherein the isothiocyano group is in either the 5- or the 6-position on the benzoxazole nucleus are preferred.

Also preferred are compounds of formula I having the structure

VIII

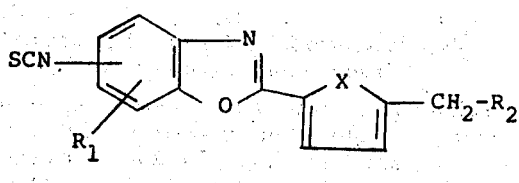

The following examples are specific embodiments of this invention.

EXAMPLE 1

5-Isothiocyanato-2-[5-(4-morpholinylmethyl)-2-thienyl]benzoxazole

A. 2-[(5-Methyl-2-thienylidene)amino]-4-nitrophenol

4Nitro-o-aminophenol (30.8 g, 0.2 mole) and 5-methyl-2-thiophenecarboxaldehyde (25.2 g, 0.2 mole) are dissolved in 250 ml of absolute ethanol and stirred at room temperature for 0.5 hour. The precipitated material is filtered and washed with additional ethanol yielding 49.8 g of product, melting point 202°–204°C.

B. 5-Nitro-2-(5-methyl-2-thienyl)benzoxazole

2-[(5-Methyl-2-thienylidene)amino]-4-nitrophenol (26.2 g, 0.1 mole) is dissolved in 500 ml of acetonitrile by heating the mixture to reflux. To this hot solution, lead tetraacetate (44.4 g, 0.1 mole) is added and heating is continued for 15 minutes. The mixture is filtered while hot, cooled to room temperature and scratched to induce crystallization. The resulting crystals are collected to yield 18.6 g of product, melting point 166°–168°C.

C. 2-(5-Bromomethyl-2-thienyl)-5-nitrobenzoxazole

To 2-(5-methyl-2-thienyl)-5-nitrobenzoxazole (5.5 g, 0.021 mole) dissolved in 125 ml of chloroform, N-bromosuccinimide (7.5 g, 0.042 mole) is added. Azobisbutyronitrile (0.25 g) is added, and the mixture is heated at reflux for 24 hours. The reaction mixture is cooled to room temperature, and the precipitated succinimide removed by filtration. The chloroform solution is then washed with two 25 ml portions of 10% sodium hydroxide. The chloroform layer is separated, dried over anhydrous magnesium sulfate and evaporated under vacuum, yielding 2.7 g of solid material. Crystallization from ethanol yields 2.4 g of solid, melting point 153°–155°C. (The yield is improved by longer refluxing (48 hours) and by adding portions of azobisbutyronitrile every 12 hours.)

D. 2-[5-(4-Morpholinylmethyl)-2-thienyl]-5-nitrobenzoxazole 2-(5-Bromomethyl-2-thienyl)-5-nitrobenzoxazole (2.0 g, 0.006 mole) and morpholine (2.6 g, 0.03 mole) are dissolved in 100 ml of benzene and heated at reflux for 36 hours. The precipitated morpholine hydrobromide is removed by filtration and the benzene is evaporated yielding an oil. Crystallization from ethanol yields 1.9 g of product, melting point 149°–151°C.

E. 5-Isothiocyanato-2-[5-(4-morpholinylmethyl)-2-thienyl]benzoxazole

To a solution of 2-[5-(4-morpholinylmethyl)-2-thienyl]-5-nitrobenzoxazole (1.75 g, 0.005 mole) in 50 ml of tetrahydrofuran, 0.2 g of platinum oxide is added. The mixture is hydrogenated at 50 psi over a period of 3 hours. The catalyst is removed by filtration and the solvent is evaporated under vacuum yielding an oil. The oil is dissolved in 25 ml of chloroform and added slowly to the following mixture at 10°C: water 25 ml; calcium carbonate 1.2 g, 0.012 mole; thiophosgene 0.6 g, 0.005 mole; and chloroform 25 ml. The reaction mixture is then stirred overnight at room temperature. The chloroform layer is separated, dried over anhydrous magnesium sulfate and evaporated under vacuum yielding a solid. Crystallization from petroleum ether yields 0.380 g of the title compound, melting point 135°–138°C.

EXAMPLE 2

5-Isothiocyanato-2-[3-(4-morpholinylmethyl)-2-thienyl]benzoxazole

A. 2-[[(3-Methyl-2-thienyl)methylene]amino]-4-nitrophenol

To a solution of 4-nitro-o-aminophenol (15.4 g, 0.1 mole) in 200 ml of ethanol, 3-methyl-2-thiophene carboxaldehyde (12.6 g, 0.1 mole) is added at room temperature. The mixture is allowed to stir for 1 hour and the precipitated yellow Schiff's Base is collected. Crystallization from acetonitrile yields 24.1 g of product, melting point 169°–171°C.

B. 5-Nitro-2-(3-methyl-2-thienyl)benzoxazole

2-[[(3-Methyl-2-thienyl)methylene]amino]-4-nitrophenol (13.1 g, 0.05 mole) is heated to reflux in 500 ml of glacial acetic acid and lead tetraacetate (22.2 g, 0.05 mole) is added to the hot mixture. After heating for 10 minutes, the mixture is diluted with 1 liter of water and the precipitated product collected. The crude material is dissolved in chloroform (350 ml) and treated with activated charcoal. The chloroform is evaporated yielding 5.4 g of product, melting point 174°–176°C.

C. 5-Nitro-2-(3-bromomethyl-2-thienyl)benzoxazole

A mixture of 5-nitro-2-(3-methyl-2-thienyl)benzoxazole (11.0 g, 0.042 mole) and N-bromosuccinimide (7.55 g, 0.042 mole) are refluxed for 36 hours in 400 ml of chloroform. Approximately every 12 hours azobisbutyronitrile (0.1 g) is added as a catalyst. The reaction mixture is cooled to room temperature and the precipitated succinimide removed by filtration. The chloroform solution is washed with 150 ml of 5% sodium hydroxide and dried over anhydrous magnesium sulfate. The chloroform is removed under vacuum yielding a solid. Crystallization from ethanol yields 8.6 g of product, melting point 146°–148°C.

D. 5-Nitro-2-[3-(4-morpholinylmethyl)-2-thienyl]-benzoxazole

A mixture of 5-nitro-2-(3-bromomethyl-2-thienyl)-benzoxazole (5.0 g, 0.0147 mole) and morpholine (2.6 g, 0.03 mole) in 200 ml of benzene is refluxed for 24 hours. The precipitated morpholine hydrobromide is removed by filtration and the benzene evaporated under vacuum yielding 4.0 g of solid. Crystallization from ethanol yields 3.4 g of product, melting point 143°–145°C.

E. 5-Isothiocyanato-2-[3-(4-morpholinylmethyl)-2-thienyl]benzoxazole

To a solution of 5-nitro-2-[3-(4-morpholinylmethyl)-2-thienyl]benzoxazole (3.2 g, 0.0093 mole) in 100 ml of tetrahydrofuran, 0.3 g of platinum oxide is added and the mixture hydrogenated at 50 psig over a period of 3 hours. The catalyst is removed by filtration and the THF evaporated under vacuum yielding the amine as an oil. The amine is dissolved in 50 ml of chloroform and added slowly to a mixture of the following at 10°C: water 30 ml; calcium carbonate (2.0 g, 0.019 mole); thiophosgene (1.07 g, 0.0093 mole); and chloroform 3 ml. The reaction mixture is then allowed to stir overnight at room temperature. The chloroform layer is separated, dried over anhydrous magnesium sulfate and evaporated under vacuum yielding a solid. Crystallization from petroleum ether yields 1.2 g of product, melting point 117°–118.5°C.

EXAMPLE 3

5-Isothiocyanato-2-[5-[(4-methyl-1-piperazinyl)-methyl]-2-thienyl]benzoxazole

A. 2-[5-[(4-Methyl-1-piperazinyl)methyl]-2-thienyl]-5-nitrobenzoxazole

2-[5-(Bromomethyl)-2-thienyl]-5-nitrobenzoxazole (1.16 g, 0.0034 mole, prepared as described in Example 1) and N-methylpiperazine (1.4 g, 0.014 mole) are dissolved in 50 ml of benzene and heated at reflux for 24 hours. The precipitated N-methylpiperazine hydrobromide is removed by filtration and the benzene removed under vacuum yielding a solid. Crystallization from ethanol yields 0.9 g of the title compound, melting point 135°–137°C.

B. 5-Isothiocyanato-2-[5-(4-methyl-1-piperazinyl)-methyl]-2-thienylbenzoxazole Following the procedure of Example 1E, but substituting 2-[5-[(4-methyl-1-piperazinyl)methyl]-2-thienyl]-5-nitrobenzoxazole for 2-[5-(4-morpholinyl-methyl)-2-thienyl]-5-nitrobenzoxazole, the title compound is obtained.

EXAMPLES 4 – 30

Following the procedure of Example 1, but substituting the compound listed in column I below for 4-nitro-o-aminophenol, the compound listed in column II below for 5-methyl-2-thiophenecarboxaldehyde, and the compound listed in column III below for morpholine, the compound listed in column IV is obtained.

| | Column I | Column II | Column III | Column IV |
|---|---|---|---|---|
| Ex. No. | | | | (position of O₂CH₂)—R |
| | 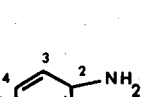 | 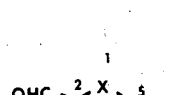 | | 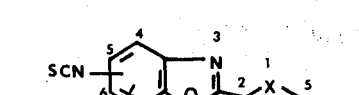 |
| 4 | 4-NO₂  R₁=H | X=S  5-CH₃ |  | 5-NCS  R₁=H  X=S   |
| 5 | 4-NO₂  R₁=H | X=O  5-CH₃ |  | 5-NCS  R₁=H  X=O   |
| 6 | 4-NO₂  R₁=H | X=O  5-CH₃ |  | 5-NCS  R₁=H  X=O   |
| 7 | 4-NO₂  R₁=H | X=S  3-CH₃ |  | 5-NCS  R₁=H  X=S   |
| 8 | 5-NO₂  R₁=H | X=S  5-CH₃ |  | 6-NCS  R₁=H  X=S   |
| 9 | 4-NO₂  R₁=5-Cl | X=S  5-CH₃ |  | 5-NCS  R₁=6-Cl  X=S   |

-continued

| | Column I | | Column II | | Column III | Column IV | | |
|---|---|---|---|---|---|---|---|---|
| Ex. No. | | | | | | (position of $O_2CH_2$)—R | | |
| 10 | 5-$NO_2$ | $R_1$=4-Cl | X=S | 5-$CH_3$ | H—N(   )N—$CH_3$ | 6-NCS | $R_1$=5-Cl | X=X | 5-N(   )N—$CH_3$ |
| 11 | 4-$NO_2$ | $R_1$=5-Cl | X=O | 5-$CH_3$ | H—N(   )N—$CH_3$ | 5-NCS | $R_1$=6-Cl | X=O | 5-N(   )N—$CH_3$ |
| 12 | 5-$NO_2$ | $R_1$=5-Cl | X=O | 5-$CH_3$ | H—N(   )N—$CH_3$ | 6-NCS | $R_1$=6-Cl | X=O | 5-N(   )N—$CH_3$ |
| 13 | 4-$NO_2$ | $R_1$=5-$CH_3$ | X=S | 5-$CH_3$ | H—N(   )N—$CH_3$ | 5-NCS | $R_1$=6-$CH_3$ | X=S | 5-N(   )N—$CH_3$ |
| 14 | 5-$NO_2$ | $R_1$=4-$CH_3$ | X=S | 5-$CH_3$ | H—N(   )N—$CH_3$ | 6-NCS | $R_1$=5-$CH_3$ | X=S | 5-N(   )N—$CH_3$ |
| 15 | 4-$NO_2$ | $R_1$=5-$CH_3$ | X=O | 5-$CH_3$ | H—N(   )N—$CH_3$ | 5-NCS | $R_1$=6-$CH_3$ | X=O | 5-N(   )N—$CH_3$ |
| 16 | 5-$NO_2$ | $R_1$=4-$CH_3$ | X=O | 5-$CH_3$ | H—N(   )N—$CH_3$ | 6-NCS | $R_1$=5-$CH_3$ | X=O | 5-N(   )N—$CH_3$ |
| 17 | 4-$NO_2$ | $R_1$=H | X=S | 5-$CH_3$ | HN(   ) | 5-NCS | $R_1$=H | X=S | 5-N(   ) |
| 18 | 4-$NO_2$ | $R_1$=H | X=O | 5-$CH_3$ | HN(   ) | 5-NCS | $R_1$=H | X=O | 5-N(   ) |
| 19 | 4-$NO_2$ | $R_1$=H | X=S | 5-$CH_3$ | HN(   )—$CH_3$ | 5-NCS | $R_1$=H | X=S | 5-N(   )—$CH_3$ |
| 20 | 4-$NO_2$ | $R_1$=H | X=O | 5-$CH_3$ | HN(   )—$CH_3$ | 5-NCS | $R_1$=H | X=O | 5-N(   )—$CH_3$ |
| 21 | 4-$NO_2$ | $R_1$=H | X=S | 5-$CH_3$ | HN(   )-$C_2H_5$ | 5-NCS | $R_1$=H | X=S | 5-N(   )-$C_2H_5$ |
| 22 | 4-$NO_2$ | $R_1$=H | X=O | 5-$CH_3$ | HN(   )-$C_2H_5$ | 5-NCS | $R_1$=H | X=O | 5-N(   )-$C_2H_5$ |
| 23 | 5-$NO_2$ | $R_1$,4-$OCH_3$ | X=S | 5-$CH_3$ | H—N(   )N—$CH_3$ | 6-NCS | $R_1$=5-$OCH_3$ | X=S | 5-N(   )N—$CH_3$ |
| 24 | 5-$NO_2$ | $R_1$=4-$OCH_3$ | X=O | 5-$CH_3$ | H—N(   )N—$CH_3$ | 6-NCS | $R_1$=5-$OCH_3$ | X=O | 5-N(   )N—$CH_3$ |
| 25 | 4-$NO_2$ | $R_1$=H | X=O | 5-$CH_3$ | H—N(   )O | 5-NCS | $R_1$=H | X=O | 5-N(   )O |
| 26 | 5-$NO_2$ | $R_1$=H | X=O | 5-$CH_3$ | H—N(   )O | 6-NCS | $R_1$=H | X=O | 5-N(   )O |
| 27 | 4-$NO_2$ | $R_1$=H | X=S | 5-$CH_3$ | H—N(   )S | 5-NCS | $R_1$=H | X=S | 5-N(   )S |
| 28 | 5-$NO_2$ | $R_1$=H | X=S | 5-$CH_3$ | H—N(   )S | 6-NCS | $R_1$=H | X=S | 5-N(   )S |
| 29 | 4-$NO_2$ | $R_1$=H | X=S | 3-$CH_3$ | H—N(   )S | 5-NCS | $R_1$=H | X=S | 3-N(   )S |
| 30 | 5-$NO_2$ | $R_1$=H | X=S | 3-$CH_3$ | H—N(   )S | 6-NCS | $R_1$=H | X=S | 3-N(   )S |

What is claimed is:

1. A compound having the structure

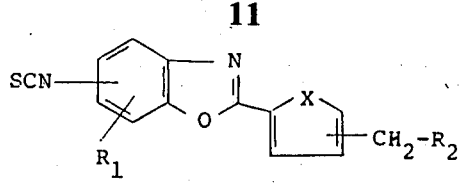

or a pharmaceutically acceptable salt thereof, wherein $R_1$ is hydrogen, alkyl, alkoxy or halogen; X is oxygen or sulfur; and $R_2$ is, 4-morpholinyl or 4-thiamorpholinyl; wherein alkyl and alkoxy are groups having 1 to 6 carbon atoms.

2. A compound in accordance with claim 1 having the structure

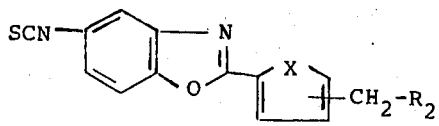

3. A compound in accordance with claim 1 having the structure

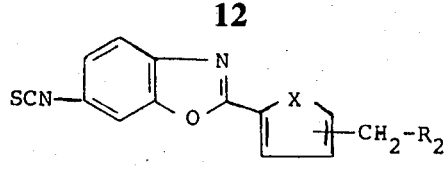

4. A compound in accordance with claim 1 having the structure

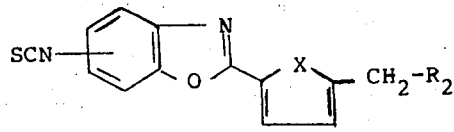

5. A compound in accordance with claim 1 wherein X is oxygen.

6. A compound in accordance with claim 1 wherein X is sulfur.

7. The compound in accordance with claim 6 having the name 5-isothiocyanato-2-[5-(4-morpholinylmethyl)-2-thienyl]benzoxazole.

8. The compound in accordance with claim 6 having the name 5-isothiocyanato-2-[3-(4-morpholinylmethyl)-2-thienyl]benzoxazole.

* * * * *

UNITED STATES PATENT AND TRADEMARK OFFICE
CERTIFICATE OF CORRECTION

PATENT NO. : 3,969,351
DATED : July 13, 1976
INVENTOR(S) : Venkatachala L. Narayanan et al.

It is certified that error appears in the above-identified patent and that said Letters Patent are hereby corrected as shown below:

Column 7, line 40, "chloroform 3" should read
-- chloroform 30 --.

Column 10, Example 10, the last structure should read $X=S$ 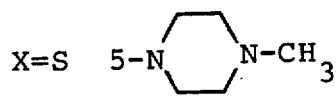

Signed and Sealed this

Thirtieth Day of November 1976

[SEAL]

Attest:

RUTH C. MASON
*Attesting Officer*

C. MARSHALL DANN
*Commissioner of Patents and Trademarks*